United States Patent [19]

Strasilla et al.

[11] 4,393,886

[45] Jul. 19, 1983

[54] MIXTURES OF QUATERNARY, POLYMERIC, HIGH MOLECULAR WEIGHT AMMONIUM SALTS, WHICH ARE BASED ON ACRYLIC COMPOUNDS, AND SURFACTANTS, THEIR PREPARATION, AND THEIR USE IN COSMETICS

[75] Inventors: Dieter Strasilla, Weil am Rhein, Fed. Rep. of Germany; Laszlo Moldovanyi, Basel, Switzerland; Charles Fearnley; Hubert Meindl, both of Riehen, Switzerland

[73] Assignee: Ciba-Geigy Corporation, Ardsley, N.Y.

[21] Appl. No.: 286,811

[22] Filed: Jul. 27, 1981

[30] Foreign Application Priority Data

Sep. 5, 1980 [CH] Switzerland ................ 6688/80

[51] Int. Cl.$^3$ .................................. A45D 7/00
[52] U.S. Cl. .................................. 132/7; 424/70
[58] Field of Search ............. 132/7; 424/70, DIG. 2

[56] References Cited

U.S. PATENT DOCUMENTS 3,313,734 4/1967 Lang et al. .
3,996,146 12/1976 Tarasov et al. .
4,009,256 2/1977 Nawak et al. .
4,027,008 5/1977 Sokol ..................... 424/DIG. 2
4,240,450 12/1980 Grollior ..................... 424/DIG. 2
4,265,782 5/1981 Armstrong ..................... 424/70

FOREIGN PATENT DOCUMENTS 1073947 6/1967 United Kingdom .
1195158 6/1970 United Kingdom .
1342176 12/1973 United Kingdom .
2027045 2/1980 United Kingdom .

Primary Examiner—G. E. McNeill
Attorney, Agent, or Firm—Edward McC. Roberts

[57] ABSTRACT

Mixtures which contain
(a) polymeric ammonium salts which are soluble or give microemulsions in aqueous surfactant systems and which can be obtained by water-in-oil emulsion polymerization or solution polymerization of a quaternary ammonium salt of the acrylic acid series and optionally at least one other acrylic monomer, and which has a molecular weight distribution of $10^4$ to $10^9$, the molecular weight of at least 5 percent of the polymer being $10^7$ to $10^9$, and
(b) a non-ionic surfactant or a surfactant with one positive and one negative charge within the molecule, can be used as cosmetics, in particular as hair cosmetics, the hair treated according to the invention having an excellent ease of dry combing and, in particular, wet combing.

17 Claims, No Drawings

MIXTURES OF QUATERNARY, POLYMERIC, HIGH MOLECULAR WEIGHT AMMONIUM SALTS, WHICH ARE BASED ON ACRYLIC COMPOUNDS, AND SURFACTANTS, THEIR PREPARATION, AND THEIR USE IN COSMETICS

The present invention relates to aqueous mixtures of polymeric, quaternary ammonium salts and surfactants, which contain (a) at least one ammonium salt which is soluble or gives a microemulsion in aqueous surfactant systems and which has a molecular weight distribution of $10^4$ to $10^9$, the molecular weight of at least 5 percent by weight of the copolymeric salt being $10^7$ to $10^9$ and the salt containing recurring structural elements of the formula

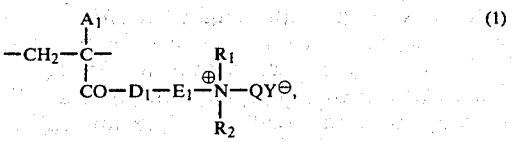

and optionally, in any order, at least one of the recurring structural elements of the formulae

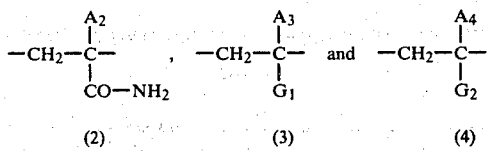

in which $A_1$, $A_2$, $A_3$ and $A_4$ are each hydrogen or methyl, $G_1$ and $G_2$ differ from one another and are each —CN, —COOH or

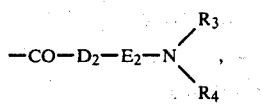

$D_1$ and $D_2$ are each oxygen or —NH—, $E_1$ and $E_2$ are each alkylene having 1 to 4 carbon atoms which is unsubstituted or substituted by hydroxyl, $R_1$, $R_2$, $R_3$ and $R_4$ are each methyl or ethyl, Q is alkyl, hydroxyalkyl having 1 to 4 carbon atoms or benzyl, and $Y^\ominus$ is a halide, alkylsulfate or alkylphosphonate anion having 1 to 4 carbon atoms in the alkyl radical, and (b) at least one non-ionic surfactant or a surfactant with one positive and one negative charge within the molecule.

The invention also relates to the preparation process for the abovementioned mixtures, their use in cosmetics, the cosmetics (hair cosmetics) which contain the mixtures according to the invention and methods of applying these cosmetics, in particular methods of treating hair, and hair treated by these methods, for example hair in the form of wigs.

The polymeric ammonium salts used as component (a) in the mixtures according to the invention are distinguished by the fact that they can be obtained by water-in-oil emulsion polymerisation or solution polymerisation of a quaternary ammonium salt of the acrylic acid series and optionally at least one other acrylic comonomer.

The water-in-oil emulsion polymerisation, which is also called inverse emulsion polymerisation, or solution polymerisation, allows the high molecular weight range of $10^7$ to $10^9$ to be achieved for the polymers used according to the invention; within the wide molecular weight distribution of $10^4$ to $10^9$, preferably 5 to 60 and in particular 20 to 50 percent by weight of the copolymers are within this high molecular weight range. Most preferably, 30 to 45 percent by weight of the copolymers are within a molecular weight range of $10^7$ to $10^9$ and less than 15 percent by weight are in a molecular weight range smaller than $10^5$.

As well as providing the molecular weight distribution, the content of structural elements of the formula (1) in the polymers, which is also called the quaternary content, is another essential characteristic of the ammonium salts used, these salts containing on average about 5 to 100, preferably 6 to 40 and in particular 10 to 30, mol % of structural elements of the formula (1), on average about 0 to 95, preferably 10 to 95 and in particular 50 to 90, mol % of structural elements of the formula (2) and on average about 0 to 10, preferably a total of 1 to 8, mol % of structural elements of the formula (3) and, optionally, (4), i.e. (3) and/or (4), and in particular in each case 1 to 4 mol % of the structural elements of the formulae (3) and (4). Ammonium salts with a quaternary content, i.e. a content of structural elements of the formula (1), of 100% are homopolymers. However, a quaternary content of 100% is to be regarded as an ideal value, since the homopolymers always contain traces (for example 0.01 to 0.5 percent by weight) of structural elements of the formula (4) in which $G_2$ is —COOH as a result of hydrolysis of the structural elements of the formula (1). Copolymers which contain at least one of the structural elements (2), (3) and/or (4) are preferred to the homopolymers as component (a) of the mixtures according to the invention.

In the formula (1), $A_1$ is preferably methyl, $D_1$ is preferably oxygen, $E_1$ is preferably unsubstituted n-propyl or, in particular, unsubstituted ethylene, $R_1$ and $R_2$ are preferably methyl and Q is preferably unsubstituted n-propyl, but preferably ethyl or, in particular, methyl. $A_2$ in formula (2) is preferably hydrogen. In formula (3), in cases where structural elements of the formula (3) are present by themselves, i.e. if no structural elements of the formula (4) are present, $A_3$ is preferably methyl and $G_1$ is preferably

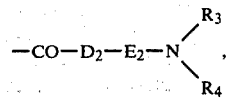

in which $D_2$, $E_2$, $R_3$ and $R_4$ are the radicals defined above as preferred for $D_1$, $E_1$, $R_1$ and $R_2$. In cases where structural elements of the formula (4) are present in addition to the structural elements of the formula (3), $A_4$ in formula (4) is preferably hydrogen and $G_2$ is preferably —CN, or $A_4$ is, in particular, methyl and $G_2$ is, in particular, —COOH.

Non-ionic surfactants for component (b) in the mixtures according to the invention are ethoxylated/propoxylated fatty alcohols, fatty amines, fatty acids, fatty acid amides, alkylphenols or carbohydrates, in which the terminal hydroxyl groups are free or etherified and, in particular, alkyl ethers having 1 to 20 carbon atoms in the ether moiety are present, adducts (block copolymers) of ethylene oxide and propylene oxide, phosphoric acid polyglycol esters or amine oxides, which preferably contain a fatty radical.

Fatty acid esters of tri-, tetra-, penta- or hexahydric alcohols (glycerol, pentaerythritol, sorbital and sorbitan) or of monosaccharides and disaccharides (sucrose) are also suitable.

The ethoxylated fatty acids, fatty alcohols, fatty acid amides, alkylphenols or carbohydrates used as non-ionic surfactants are preferably those of one of the formulae

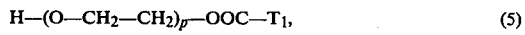 (5)

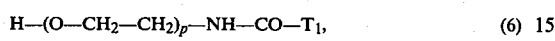 (6)

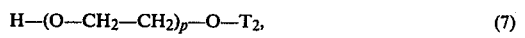 (7)

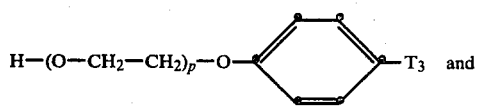 (8)

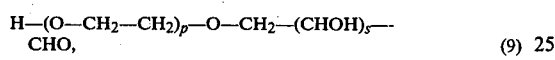 (9)

in which $T_1$ is alkyl or alkenyl having 7 to 21, preferably 11 to 17, carbon atoms, $T_2$ is alkyl or alkenyl having 8 to 22, preferably 12 to 18, carbon atoms, $T_3$ is alkyl having 6 to 14, preferably 8 to 12, carbon atoms, p is an integer from 1 to 50, preferably 1 to 20, and s is 3 or, preferably, 4.

In formula (5), the radicals $T_1COO-$ are derived from the corresponding saturated or unsaturated fatty acids having 8 to 22, preferably 12 to 18, carbon atoms. Examples of the corresponding fatty acids are caprylic, capric, arachic and behenic acid, and in particular lauric, myristic, palmitic and stearic acid, or myristoleic, palmitoleic, elaeostearic and clupanodonic acid, and in particular oleic, elaidic, erucic, linoleic and linolenic acid. Alkyl and alkenyl radicals $T_1$ which are derived from industrial mixtures of the saturated and/or unsaturated fatty acids mentioned are particularly preferred. The fatty alcohol radicals and fatty acid amide radicals $T_1-CO-NH-$ and $T_2-O-$ in the formulae (6) and (7) are preferably derived from the corresponding abovementioned fatty acids.

Preferred alkyl radicals $T_2$ in formula (8) are, for example, alkyl radicals having 6 to 12 carbon atoms, such as hexyl, i-hexyl, heptyl, i-octyl and dodecyl, and also alkyl radicals which have 12 to 14 carbon atoms and are derived from dimerised olefines having in each case 6 or 7 carbon atoms.

Ethoxylated carbohydrates are, depending on the value of s in formula (9), in particular ethoxylated pentoses, and especially hexoses, for example ethoxylated glucose.

The ethoxylated surfactants of the formulae (5) to (9) can in some cases also be present in etherified form (alkyl ethers having 1 to 20 carbon atoms in the ether moiety).

Preferred ethoxylated, non-ionic surfactants of the formulae (5) to (9) are the ethoxylated fatty acids and fatty alcohols of the formulae (5) and (7), and in particular the ethoxylated alkylphenols of the formula (8). A specific example of such ethoxylated alkylphenols is, inter alia, the surfactant of the formula

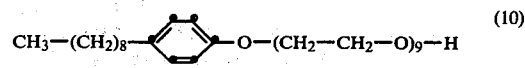 (10)

Commercially available products of ethylene oxide and propylene oxide which can be obtained by addition of ethylene oxide onto a condensation product of propylene oxide and propylene glycol and which have molecular weights of about 1,000 to about 15,000 are also preferred non-ionic surfactants for component (b) of the mixture according to the invention. Such adducts are block copolymers which have the probable formula

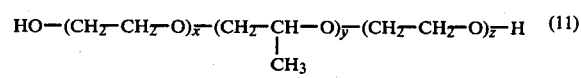 (11)

in which x, y and z are identical or different integers. The values of x, y and z depend on the molecular weight of the copolymer and are only average values. Particularly preferred copolymers are those having average molecular weights of 2,000 to 8,000 and in which the average values of x and z in each case vary between 20 and 60 and that of y between 20 and 80, and thus have the probable formula

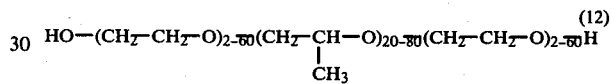 (12)

Non-ionic surfactants for component (b) are also phosphoric acid polyglycol esters and amine oxides, in particular those with fatty radicals, the phosphoric acid polyglycol esters preferably being those of the formula

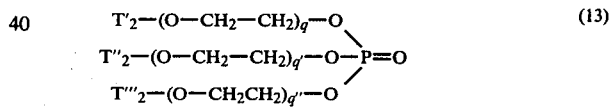 (13)

in which $T_2'$, $T_2''$ and $T_2'''$ are different or, preferably, identical and are each alkyl having 6 to 14 carbon atoms and q, q' and q'' are different or, preferably, identical and are in each case an integer from 6 to 12, and the amine oxides preferably being those of one of the formulae

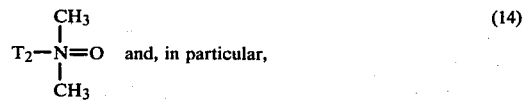 (14)

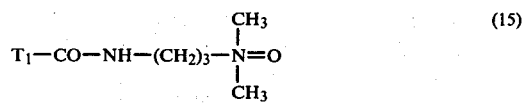 (15)

in which $T_1$ and $T_2$ are as defined.

Fatty acid esters of tri-, tetra-, penta- or hexahydric alcohols having 3 to 6 carbon atoms or of monosaccharides or disaccharides (sucrose) are also suitable. The fatty acid radicals are derived, for example, from saturated or unsaturated fatty acids having, preferably, 12 to 18 carbon atoms (lauric acid, palmitic acid, stearic acid or oleic acid). The esters are, in particular, sorbitan fatty acid esters.

The non-ionic surfactants of the formulae (5) to (12), in particular of the formulae (5), (7), (8) and (11), and especially (10) and (12), are preferable to the non-ionic surfactants of the formulae (13) to (15).

Component (b) can also be a surfactant which has one positive and one negative charge within the molecule, these surfactants generally being preferable to the non-ionic surfactants of the type described. These surfactants are, in particular, betaines or sulfobetaines, which are derived from imidazoline derivatives or open-chain aliphatic amines.

The betaines or sulfobetaines which are derived from imidazoline derivatives and are used, according to the invention, as component (b) are preferably those of one of the formulae

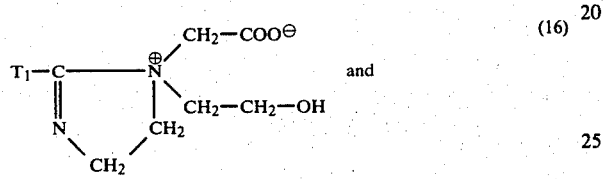 (16)

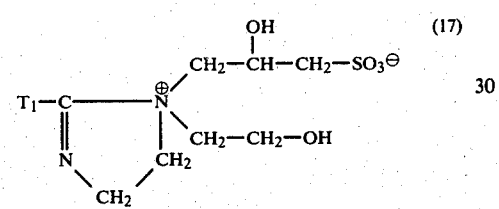 (17)

in which $T_1$ is as defined.

Examples of specific representatives of such imidazolinium betaines or sulfobetaines are, inter alia, the surfactants of the formulae

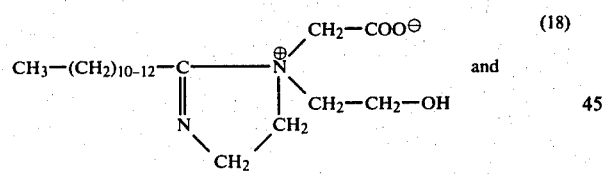 (18)

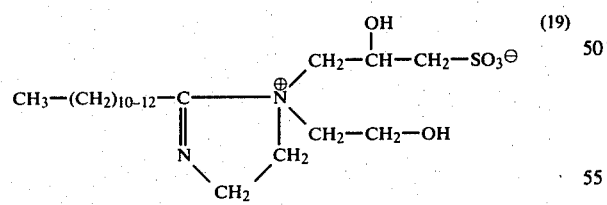 (19)

or industrial surfactant mixtures thereof.

The betaine derivatives which are derived from an open-chain aliphatic amine and are used according to the invention are preferably those of one of the formulae

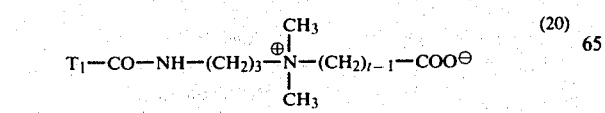 (20)

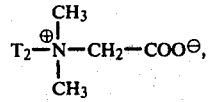 (21)

$T_2-N^{\oplus}H_2-CH_2-(CH_2)_{t-1}-COO^{\ominus}$ (22)

$T_2-(NH-CH_2-CH_2)_{t-1}-NH-CH_2-CH_2-N^{\oplus}H_2-CH_2-COO^{\ominus}$ (23)

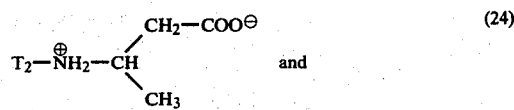 (24)

 (25)

in which $T_1$ and $T_2$ are as defined and t is 1 or 2.

Examples of specific representatives of such betaine derivatives are, inter alia, the surfactants of the formulae

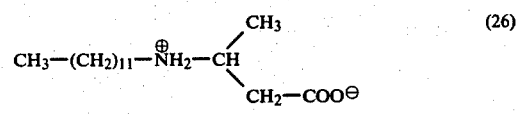 (26)

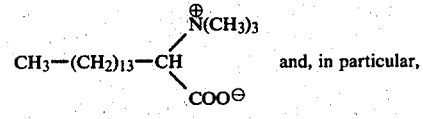 (27)

$CH_3-(CH_2)_{11-13}-N^{\oplus}H_2-(CH_2)_2-COO^{\ominus}$ (28)

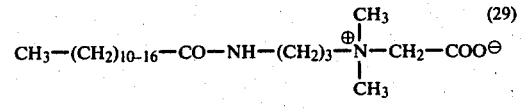 (29)

$CH_3-(CH_2)_{10-12}-CH_2-N^{\oplus}H_2-(CH_2)_2COO^{\ominus}$ and (30)

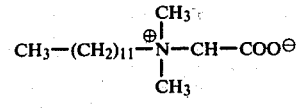 (31)

and industrial surfactant mixtures thereof.

The sulfobetaine derivatives which are derived from an aliphatic, open-chain amine and are used according to the invention are preferably those of one of the formulae

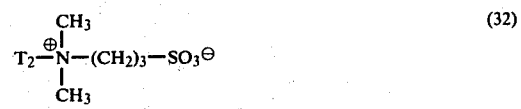 (32)

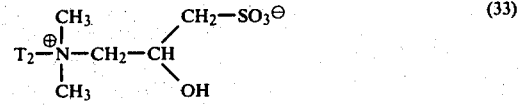 (33)

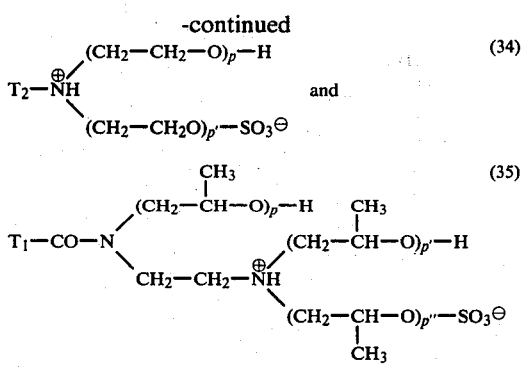

in which $T_1$ and $T_2$ are as defined and p′ and p″ have the values as defined for p, with p, p′ and p″ being identical or different.

Examples of specific representatives of such sulfobetaine derivatives are, inter alia, the surfactants of the formulae

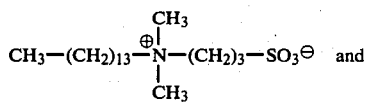

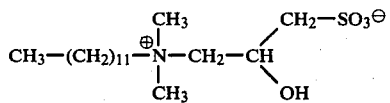

Components (b) of the mixture according to the invention which are of particular interest are non-ionic surfactants of the formulae (12) and, in particular, (10), and especially surfactants of the formulae (18), (19) and (28) to (31) which have one positive and one negative charge within the molecule.

The mixtures according to the invention contain components (a) and (b) in a weight ratio of (a):(b) of generally 1:2 to 400, preferably 1:4 to 100 and in particular 1:10 to 50.

For the preparation of the mixtures according to the invention, for example, a procedure is followed in which a monomer of the formula

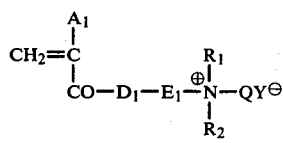

, and, if desired, at least one comonomer of one of the formulae

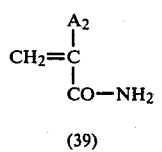 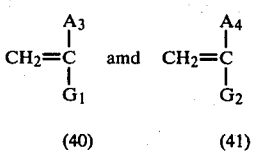

in which $A_1$, $A_2$, $A_3$, $A_4$, $D_1$, $E_1$, $G_1$, $G_2$, $R_1$, $R_2$, Q and $Y^\ominus$ are as defined, are copolymerised by water-in-oil emulsion polymerisation in the presence of a water-in-oil emulsifier and optionally an emulsion stabiliser and a polymerisation initiator, and the polymer is precipitated with a solvent which is as a rule miscible with oil and water, and is then dried, the preparation process comprising using the resulting polymer as component (a) and mixing the polymer with at least one non-ionic surfactant or a surfactant which has one positive and one negative charge within the molecule, as component (b), in an aqueous medium at room temperature and at a pH value from 5 to 9. If the solution polymerisation method is used, it is not necessary to employ emulsifiers and emulsion stabilisers. Water is as a rule used as the solvent.

Hydrophobic, organic liquids are required for the oil phase in the water-in-oil emulsion polymerisation. Suitable liquids for this purpose are, for example, aliphatic or aromatic hydrocarbons, oils of animal or vegetable origin and the corresponding denatured oils (for example hydrogenated oils or polymerised oils). Preferred hydrophobic organic liquids are aliphatic hydrocarbons, such as kerosene, paraffin and isoparaffin, and aromatic hydrocarbons, such as benzene, toluene and xylene. Commercially available industrial mixtures of preferably branched paraffin oils with a boiling range from 160° to 260° C., preferably 180° to 210° C., are of particular interest.

Water-in-oil emulsifiers which are used in the inverse emulsion polymerisation are polyoxyalkylene adducts, preferably polyoxyethylene adducts, of aliphatic alcohols having 8 to 24 carbon atoms, such as lauryl, cetyl, stearyl and oleyl alcohols, of fatty acids of the above-mentioned type having 8 to 24 carbon atoms, preferably lauric, palmitic, stearic and oleic acid, of alkylphenols having 8 to 24 carbon atoms in the alkyl radical, for example octyl-, nonyl-, dodecyl- and dinonyl-phenol, and of esters of fatty acids of the type mentioned and polyhydric alcohols, for example glycerol, pentaerythritol, sorbitol and sorbitan. Commercially available mixtures, i.e. polyoxyalkylene adducts of industrial alcohol mixtures, fatty acid mixtures, alkylphenol mixtures and ester mixtures, are also particularly suitable water-in-oil emulsifiers. However, esters of fatty acids of the type mentioned or of fatty acid mixtures and polyhydric alcohols of the type mentioned are particularly preferred, sorbitan monooleate being of special interest.

In particular cases, it has proved advantageous to use an emulsion stabiliser in the oil phase. Stabilisers which are suitable for this purpose are, in particular, rubbers which are soluble in the oil phase, including both rubbers of natural origin, for example crystal gum, and, preferably those of synthetic origin, for example polybutadiene, styrene/butadiene copolymers and, in particular, polyisoprene. Polyisoprene is of special interest.

As a rule, the oil phase contains about 2 to 15 percent by weight of emulsifier and 0 to about 1, preferably 0.4 to 0.8, percent by weight of stabiliser.

After the oil phase has been mixed with the aqueous phase, which contains the monomers of the formula (38) and optionally the comonomers of the formulae (39), (40) and (41), the polymerisation reaction is as a rule started by adding a polymerisation initiator. The initiators employed can be the usual polymerisation catalysts, preferably in the form of an organic or aqueous solution, for example azo compounds, such as azo-bis-(isobutyronitrile) or azo-bis(dimethylvaleronitrile), oxidising agents, preferably peroxides, such as hydrogen peroxide or benzoyl peroxide, or, preferably, persulfates, such as ammonium persulfate, and also chlorates or chromates, reducing agents, such as sulfites, bisulfites, oxalic acid and ascorbic acid, and combinations of the abovementioned oxidising and reducing agents, as so-called redox catalysts. In the present case, sodium sulfite, preferably as an aqueous solution, is a particularly suitable initiator.

The polymerisation reaction as a rule takes place at 30° to 90° C., preferably 40° to 70° C., and proceeds as an exothermic reaction, so that it may be necessary to maintain the polymerisation temperature by cooling.

For the usual working-up of the product, the resulting polymer is as a rule precipitated by a solvent which is preferably miscible with oil and water, for example methanol, isopropanol or acetone, the precipitation generally being carried out by adding the water-in-oil emulsion to the solvent previously introduced, preferably at room temperature (15° to 25° C.), after which the polymer which has precipitated is filtered off and dried, preferably at temperatures of at most 60° C. and in particular at temperatures from about 30° to 50° C., reduced pressure being advantageous.

The resulting water-in-oil homopolymers or, preferably, copolymers known per se are then mixed as component (a) by methods known per se with component (b) in an aqueous medium, preferably at room temperature (15° to 25° C.) and at a pH value of 5 to 9, in order to obtain the novel mixtures according to the invention.

In the cosmetics industry, the mixtures, according to the invention, of components (a) and (b) are preferably used as hair cosmetics.

In their preferred embodiment, the cosmetics, preferably hair cosmetics, according to the invention are in the form of aqueous solutions which contain, for example, 0.05 to 1.5, preferably 0.2 to 1.0, parts by weight, calculated as effective substance, of at least one polymeric ammonium salt having structural elements of the formula (1) and optionally (2), (3) and/or (4), 5 to 20, preferably 8 to 15 and in particular 9 to 12, parts by weight, calculated as effective substance, of at least one non-ionic surfactant or one surfactant which has one positive and one negative charge within the molecule, as component (b), and optionally cosmetic assistants, as component (c), and are diluted with demineralised water to a total of 100 parts by weight.

The cosmetic assistants which may be present as component (c) are commercially available agents such as are used in hair cosmetics. These agents are, for example, surfactants other than the surfactants of the type described which are used as component (b), such as polyglycerol esters and polyglycol esters of fatty acids, in particular polyglycerol oleates and also polyglycols and foam stabilisers, for example fatty acid polyalkanolamides, thickeners of natural or synthetic origin, such as hydroxypropylmethylcellulose and polyacrylic acid, opalising agents, such as fatty acid monoalkanolamides or, preferably, glycerol monostearate, and also, inter alia, preservatives, perfumes and pearlescent agents.

If required, the hair cosmetics are adjusted to a pH value of 5 to 8, preferably 7.0 to 7.5 or even more preferably, 7.0 to 7.2, which can advantageously be achieved by addition of aqueous solutions of, for example, sodium hydroxide or citric acid.

When the aqueous hair cosmetic described above is used for hair treatment, preferably on human hair, it is applied to hair which has been wetted with tapwater, as a rule at room temperature or slightly elevated temperature, for example 20° to 40° C., and the hair is then shampooed and conditioned. The hair treated in this way can also be in the form of wigs or toupees.

The essential advantage of the present invention is that application of the hair cosmetics which contain, as component (a), the polymeric, quaternary ammonium salts used, having structural elements of the formula (1) and optionally (2), (3) and (4), from the corresponding water-in-oil homopolymers or, preferably, copolymers with high molecular weight portions and, as component (b), surfactants of the type described, gives the treated hair excellent ease of combing when dry and, in particular, when wet. In particular, the ease of wet combing of hair treated with the hair cosmetics according to the invention is clearly superior to that of hair treated with conventional cosmetics. The latter indeed also contain mixtures of surfactants and polymers, but the polymers have a different composition and, in particular, they lack the high molecular weight portions.

In the preparation instructions and examples which follow, parts and percentages are by weight.

Preparation instructions for component (a) (water-in-oil emulsion copolymers)

Instructions A: The following three solutions are prepared in an oxygen-free, inert nitrogen atmosphere:

Solution I (oil phase)

500 parts of a branched paraffin oil (industrial mixture, molecular weight: 171, boiling range: 188°–206° C.) are introduced into a double-walled reaction vessel. 140 parts of a 2.5% solution of a synthetic polyisoprene rubber (emulsion stabiliser) in paraffin oil of the type described and then 78 parts of sorbitan monooleate (water-in-oil emulsifier) are added to the paraffin oil at 20° C., with stirring.

A clear, yellowish solution is obtained.

Solution II (aqueous phase)

568.6 parts (8 mols) of acrylamide are dissolved in 700 parts of demineralised, oxygen-free water at 20° C. 220 parts of sodium chloride are introduced into this solution, with stirring, and 1,133.2 parts of a 50% aqueous solution of methacryloyloxyethyl-trimethylammonium methyl-sulfate (2 mols) are then added.

A clear, colourless solution is obtained.

Solution III (initiator solution)

0.66 part of sodium sulfite is dissolved in 40 parts of demineralised, oxygen-free water.

Copolymerisation reaction

Solution II is added to the previously introduced solution I at 20° C. in an inert nitrogen atmosphere in the course of 10 minutes, with intensive stirring (3,000 rpm). A homogeneous, white emulsion is obtained, and stirring is continued at 20° C. until the viscosity of a sample of the emulsion is 14,000 mPa.s (Brookfield Viscosimeter LV, spindle 3, 6 rpm, 25° C.), which generally takes 10 minutes. Thereafter, the reaction mixture is heated to 40° C. in the course of 30 minutes, with stirring at 300 rpm. Solution III is now added to the reaction mixture by means of a metering pump in the course of 150 minutes, the temperature being kept at 40° to 41° C. by cooling. When the initiator solution has been added, stirring of the reaction mixture is continued at 40° C. and 300 rpm until the viscosity of a sample of the emulsion has fallen to 7,600 mPa.s (Brookfield Viscosimeter LV, spindle 1, 60 rpm, 25° C.), which generally takes one hour.

Working-up

The resulting emulsion of the copolymer is poured into 24,000 parts of acetone at 20° C., with stirring, and the copolymer is precipitated. The precipitated copolymer is filtered off and dried at 40° C. under reduced pressure for 2 days. 1,100 parts of a copolymer which contains, in any order, 80 mol % of structural elements of the formula $$-CH_2-CH- \quad (42)$$
$$\quad\quad | $$
$$\quad\quad CO-NH_2$$

and 20 mol % of structural elements of the formula $$\quad\quad CH_3 \quad (43)$$
$$-CH_2-C-$$
$$\quad\quad |$$
$$\quad\quad COO-(CH_2)_2-N^{\oplus}(CH_3)_3 CH_3SO_4^{\ominus}$$

are obtained. 37% of the copolymer has a molecular weight between $10^7$ and $10^9$.

Instructions B

The procedure described in instructions A is repeated, using 1,108 parts of a 40% aqueous solution of methacryloyloxypropyl-trimethylammonium chloride (2 mols) in the aqueous phase (solution II).

1,000 parts of a copolymer which contains, in any order, 80 mol % of structural elements of the formula (42) given in instructions A and 20 mol % of structural elements of the formula $$\quad\quad CH_3 \quad (44)$$
$$-CH_2-C-$$
$$\quad\quad |$$
$$\quad\quad COO-(CH_2)_3-N^{\oplus}(CH_3)_3 Cl^{\ominus}$$

are obtained. 27% of the copolymer has a molecular weight between $10^7$ and $10^9$.

Instructions C

The procedure described in instructions A is repeated, using 1,471.5 parts of a 40% aqueous solution of methacryloyloxypropyl-dimethyl-n-propylammonium bromide (2 mols) in the aqueous phase (solution II).

1,000 parts of a copolymer which contains, in any order, 80 mol % of structural elements of the formula (42) given in instructions A and 20 mol % of structural elements of the formula $$\quad\quad CH_3 \quad\quad\quad\quad\quad\quad\quad\quad\quad (45)$$
$$-CH_2-C- \quad\quad\quad CH_3$$
$$\quad\quad | \quad\quad\quad\quad\quad |$$
$$\quad\quad COO-(CH_2)_3-N^{\oplus}(CH_2)_2-CH_3 Br^{\ominus}$$
$$\quad\quad\quad\quad\quad\quad\quad\quad |$$
$$\quad\quad\quad\quad\quad\quad\quad\quad CH_3$$

are obtained. 22% of the copolymer has a molecular weight between $10^7$ and $10^9$.

Instructions D

The procedure described in instructions A is repeated, employing the following solutions I, II and III and using 40,000 parts of acetone in the working-up operation.
Solution I 825 parts of the paraffin oil described in instructions A, 269 parts of 2.5% rubber solution described in instructions A and 255 parts of sorbitan monooleate.
Solution II An aqueous solution of 681.6 parts (9.6 mols) of acrylamide, 34.6 parts (0.48 mol) of acrylic acid, 50.3 parts (0.32 mol) of ethyl dimethylamino-methacrylate and 220 parts of sodium chloride in 700 parts of water, and an aqueous solution of 1,586.5 parts (5.6 mols) of methacryloyloxyethyl-trimethylammonium methyl-sulfate in 3,100 parts of water.
Solution III 1.07 parts of sodium sulfite in 66.8 parts of water.

2,100 parts of a copolymer which contains, in any order, 60 mol % of structural elements of the formula (42) given in instructions A, 35 mol % of structural elements of the formula (43) given in instructions A, 3 mol % of structural elements of the formula $$-CH_2-CH- \quad (46)$$
$$\quad\quad |$$
$$\quad\quad COOH$$

and 2 mol % of structural elements of the formula $$\quad\quad CH_3 \quad (47)$$
$$-CH_2-C-$$
$$\quad\quad |$$
$$\quad\quad COO-(CH_2)_2-N(CH_3)_2$$

are obtained. 12% of the copolymer has a molecular weight between $10^7$ and $10^9$.

Instructions E

The procedure described in instructions A is repeated, employing the following solutions I, II and III and using 50,000 parts of acetone in the working-up operation.
Solution I*

1,628 parts of the paraffin oil described in instructions A and 191 parts of sorbitan monooleate.
(* In contrast to instructions A, contains no rubber solution.)
Solution II A solution of 1,516.6 parts (21.36 mols) of acrylamide, 679.9 parts (2.40 mols) of methacryloyloxyethyl-trimethylammonium methyl-sulfate, 37.7 parts (0.24 mol) of ethyl dimethylamino-methacrylate and 600 parts of sodium chloride** in 2,550 parts of water.
(** In contrast to instructions A, these components are not introduced separately.)
Solution III 1.6 parts of sodium sulfite in 720 parts of water.

1,890 parts of a copolymer which contains, in any order, 90 mol % of structural elements of the formula (42) given in instructions A, 9 mol % of structural elements of the formula (43) given in instructions A and 1 mol % of structural elements of the formula (47) given in instructions D are obtained. 23% of the copolymer has a molecular weight between $10^7$ and $10^9$.

Instructions F

The procedure described in instructions A is repeated, employing the following solutions I, II and III and using 5,000 parts of acetone in the working-up operation.
Solution I 319 parts of the paraffin oil described in instructions A, 91 parts of the 2.5% rubber solution described in instructions A and 48 parts of sorbitan monooleate.
Solution II An aqueous solution of 85.3 parts (1.2 mols) of acrylamide, 2,720.2 parts of a 50% aqueous solution of methacryloyloxyethyl-trimethylammonium methyl-sulfate (4.8 mols) and 475 parts of water (in contrast to instructions A, solution II contains no sodium chloride).
Solution III 0.4 part of sodium sulfite in 25 parts of water.

1,300 parts of a copolymer which contains, in any order, 20 mol % of structural elements of the formula (42) given in instructions A and 80 mol % of structural elements of the formula (43) given in instructions A are obtained. 12% of the copolymer has a molecular weight between $10^7$ and $10^9$.

Instructions G

The procedure described in instructions A is repeated, employing the following solutions I, II and III and using 5,000 parts of acetone in the working-up operation.
Solution I 319 parts of the paraffin oil described in instructions A, 91 parts of the 2.5% rubber solution described in instructions A and 48 parts of sorbitan monooleate.
Solution II An aqueous solution of 68 parts of a 50% aqueous solution of methacryloyloxyethyl-trimethylammonium methylsulfate in 475 parts of water (in contrast to instructions A, solution II contains neither acrylamide nor sodium chloride).
Solution III 0.4 parts of sodium sulfite in 25 parts of water.

30 parts of a homopolymer which contains structural elements of the formula (43) given in instructions A and, as a result of hydrolysis, traces (0.001 to 0.5%) of structural elements of the formula (47) given in instructions D are obtained. 8% of the homopolymer has a molecular weight between $10^7$ and $10^9$.

Preparation instructions for a solution copolymer

Instructions H: The following two solutions are prepared in an oxygen-free inert nitrogen atmosphere:

Solution I (monomer solution)

71.1 parts (1 mol) of acrylamide and 141.7 parts (0.25 mol) of a 50% aqueous solution of methacryloyloxyethyl-trimethylammonium methyl-sulfate are dissolved in 228 parts of demineralised, oxygen-free water in a double-walled vessel at 20° C.

A clear colourless solution is obtained.
Solution II (initiator solution)

0.2 part of ammonium peroxodisulfate is dissolved in 150 parts of demineralised, oxygen-free water.
Copolymerisation reaction Half of solution II is added to the previously introduced solution I at 35° C. in an inert nitrogen atmosphere in the course of 1 minute with stirring. After 6 hours, the reaction solution is warmed to 50° C. and the second half of solution II is added. The mixture is stirred for 2 to 3 hours until a highly viscous solution has formed. The reaction mixture is left to stand, without stirring. After 24 hours, the resulting colourless gel is allowed to cool.
Working-up The gel is comminuted, and dissolved in 1,350 parts of demineralised water. The highly viscous solution is then pressed as a thin strand at 20° C. into 18,000 parts of acetone, and the copolymer is precipitated. It is then filtered off and kneaded again in 1,800 parts of acetone until it becomes hard and brittle. It is again filtered off, and is dried under reduced pressure at 40° C. for 2 days. 110 parts of a copolymer which contains, in any order, 80 mol % of structural elements of the formula

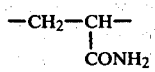

and 20 mol % of structural elements of the formula

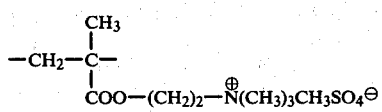

are obtained. 12% of the copolymer has a molecular weight between $10^7$ and $10^9$.

EXAMPLE 1

1.4 parts of the polymeric ammonium salt according to instructions A are introduced in small portions into 100 parts of water at 25° to 35° C. A viscous solution is formed. 20 parts of an industrial surfactant mixture of the abovementioned formula (28) are dissolved in 1,000 parts of water at 25° C. These two solutions are now mixed with one another at 25° C. The pH value of this mixture, which contains 0.7% of the ammonium salt and 10% of the surfactant, is 6.3, and is adjusted to 7.1 by addition of a 5% sodium hydroxide solution. The neutralised mixture, which is in the form of a clear aqueous solution, applied to a wig, which has been damped with tap-water, of unbleached, undyed, brown human hair of European origin by three applications in the so-called half-head test at 30° C., after which the hair of the wig is shampooed and conditioned at this temperature. In the half-head test, only one half of the wig is shampooed and conditioned with the solution described above, whilst the other half of the wig is shampooed under the same conditions but using a solution containing just the surfactant and not the inventive mixture of the ammonium salt and the surfactant. In this so-called blank formulation, the amount of ammonium salt is replaced by the corresponding amount of surfactant, so that, for example, as a comparison, the blank formulation contains 10.7% of surfactant mixture of the abovementioned formula (28), the pH value of the blank formulation likewise being adjusted to 7.0 with the aqueous 30% sodium hydroxide solution. After each application, the ease of wet and dry combing of the half of the wig treated according to the invention is evaluated in comparison with the half of the wig treated with the blank formulation, the following scale of ratings being used:

+3 much better than the blank formulation
+2 better than the blank formulation
+1 somewhat better than the blank formulation
0 no different from the blank formulation
−1 somewhat poorer than the blank formulation
−2 poorer than the blank formulation
−3 much poorer than the blank formulation.

The wet combing ratings are +2 after the 1st application and in each case +3 after the 2nd and 3rd applications, and the dry combing ratings are in each case +1 after the 1st and 2nd applications and +(1-2) after the 3rd application.

A similar improvement is achieved, when 1.4 parts of the copolymer according to instructions H are used instead of the polymeric ammonium salt according to instructions 1.

EXAMPLES 2 TO 11

The procedure described in Example 1 is repeated, the ammonium salts and surfactants (or industrial surfactant mixtures) used for the preparation of the mixture according to the invention, their concentration in the mixture, the pH value of the mixture before it is neutralised to pH 7.0 to 7.2 with the 5% sodium hydroxide solution or an aqueous 5% citric acid solution and the resulting combing ratings when the mixture is applied to human hair in the half-head test described above being summarised in Table I which follows.

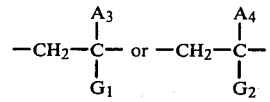

in which $A_1$, $A_2$, $A_3$ and $A_4$ are each hydrogen or methyl, $G_1$ and $G_2$ differ from one another and are each —CN, —COOH or

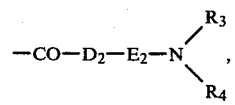

$D_1$ and $D_2$ are each oxygen or —NH—, $E_1$ and $E_2$ are each alkylene having 1 to 4 carbon atoms which is unsubstituted or substituted by hydroxyl, $R_1$, $R_2$, $R_3$ and

TABLE I

| Example No. | Ammonium salt according to instructions | Surfactant of the formula | Content of ammonium salt in the mixture % | Content of surfactant in the mixture % | pH of the mixture before neutralisation | Combing ratings W = wet combing rating D = dry combing rating after the 1st application | after the 2nd application | after the 3rd application |
|---|---|---|---|---|---|---|---|---|
| 2 | E | (29) | 0.7 | 10 | 6.2 | W +1<br>D +2 | W +1<br>D +2 | W +(1-2)<br>D +(1-2) |
| 3 | F | (29) | 0.7 | 10 | 6.2 | W +3<br>D +2 | W +3<br>D +2 | W +3<br>D +2 |
| 4 | F | (29) | 0.2 | 10 | 6.2 | W +1<br>D +1 | W +(1-2)<br>D +1 | W +(1-2)<br>D +1 |
| 5 | G | (30) | 0.7 | 10 | 4.9 | W +1 | W +1 | W +1 |
| 6 | G | (12) | 0.9 | 10 | 5.1 | W +(1-2)<br>D +(1-2) | W +1<br>D +1 | W +(1-2)<br>D +1 |
| 7 | D | (10) | 0.6 | 10 | 6.5 | W +2<br>D +2 | W +2<br>D +2 | W +2<br>D +2 |
| 8 | B | (10) | 1.0 | 10 | 6.5 | W +1<br>D +(1-2) | W +1<br>D +1 | W +1<br>D +1 |
| 9 | C | (18) | 0.7 | 10 | 7.5 | W +2<br>D +1 | W +2<br>D +1 | W +(1-2)<br>D +2 |
| 10 | E | (19) | 0.7 | 10 | 6.4 | W +1<br>D +1 | W +(1-2)<br>D +1 | W +(1-2)<br>D +1 |
| 11 | A | (31) | 0.7 | 10 | 5.3 | W +(1-2)<br>D +1 | W +1<br>D +2 | W +(1-2)<br>D +1 |

What is claimed is:

1. A cosmetic composition which contains water, (a) at least one ammonium salt which is soluble or gives a microemulsion in aqueous surfactant systems and which has a molecular weight distribution of $10^4$ to $10^9$, the molecular weight of at least 5 percent by weight of the copolymeric salt being $10^7$ to $10^9$ and the salt containing on average 5 to 100 mole % of recurring structural elements of the formula

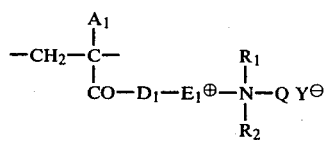

and O to an average 95 mole % of recurring structural elements of the formula

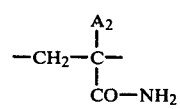

and O to an average 10 mole % of recurring structural elements of the formulas $R_4$ are each methyl or ethyl, Q is alkyl, hydroxyalkyl having 1 to 4 carbon atoms or benzyl, and $Y^-$ is a halide, alkylsulfate or alkylphosphonate anion having 1 to 4 carbon atoms in the alkyl radical, and (b) at least one non-ionic surfactant or a surfactant with one positive and one negative charge within the molecule, wherein the composition contains components (a) and (b) in a weight ratio of 1:2 to 400.

2. A composition of claim 1, which contains, as component (a), an ammonium salt which can be obtained by water-in-oil emulsion polymerisation or solution polymerisation of a quaternary ammonium salt of the acrylic acid series and, optionally at least one other acrylic monomer.

3. A composition of claim 1, wherein the molecular weight of 5 to 60 percent by weight of the polymeric salt of component (a) is $10^7$ to $10^9$.

4. A composition of claim 1, which contains, as the non-ionic surfactant for component (b), an ethoxylated fatty acid, fatty alcohol, fatty acid amide, alkylphenol or carbohydrate, an adduct of ethylene oxide and propylene oxide, a phosphoric acid polyglycol ester or an amine oxide.

5. A composition of claim 4, which contains, as component (b), an ethoxylated fatty acid, fatty alcohol, fatty acid amide, alkylphenol or carbohydrate of the formula

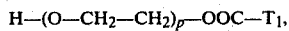

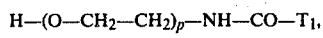

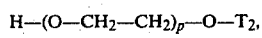

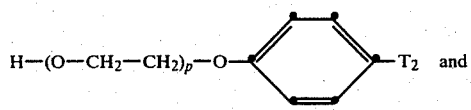

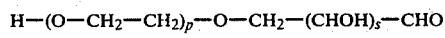

in which $T_1$ is alkyl or alkenyl having 7 to 21 carbon atoms, $T_2$ is alkyl or alkenyl having 8 to 22 carbon atoms, $T_3$ is alkyl having 6 to 14 carbon atoms, p is an integer from 1 to 50 and s is 3 or 4.

6. A composition of claim 4, which contains, as component (b), an adduct of ethylene oxide and propylene oxide, of the formula

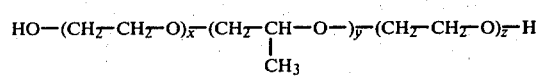

in which x, y and z are identical or different integers, the adduct having a molecular weight of 1,000 to 15,000.

7. A composition of claim 4, which contains, as component (b), a phosphoric acid polyglycol ester of the formula

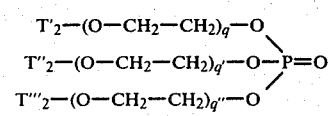

in which $T_2'$, $T_2''$ and $T_2'''$ are each alkyl having 6 to 14 carbon atoms and q, q' and q'' are each an integer from 6 to 12.

8. A composition of claim 4, which contains, as component (b), an amine oxide of the formula

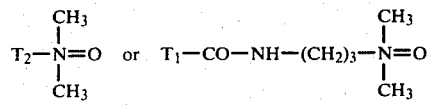

in which $T_1$ is alkyl or alkenyl having 7 to 21 carbon atoms and $T_2$ is alkyl or alkenyl having 8 to 22 carbon atoms.

9. A composition of any one of claims 1, 2 or 3, which contains, as the surfactant with one positive and one negative charge within the molecule, for component (b) a betaine or sulfobetaine which is derived from an imidazoline derivative or an open-chain, aliphatic amine.

10. A composition of claim 9, which contains, as component (b), a betaine or sulfobetaine which is derived from an imidazoline derivative and has the formula

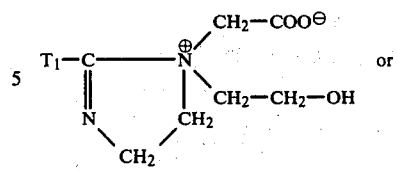

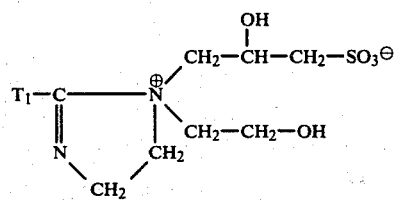

in which $T_1$ is alkyl or alkenyl having 7 to 21 carbon atoms.

11. A composition of claim 9, which contains, as component (b), a betaine derivative which is derived from an open-chain aliphatic amine and has the formula

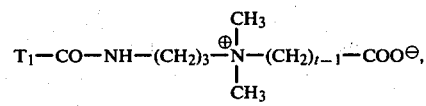

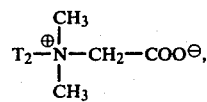

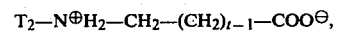

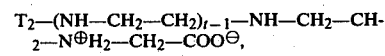

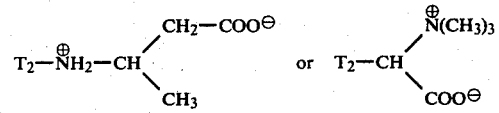

in which $T_1$ is alkyl or alkenyl having 7 to 21 carbon atoms, $T_2$ is alkyl or alkenyl having 8 to 22 carbon atoms and t is 1 or 2.

12. A composition of claim 9, which contains, as component (b), a sulfobetaine derivative which is derived from an open-chain, aliphatic amine and has the formula

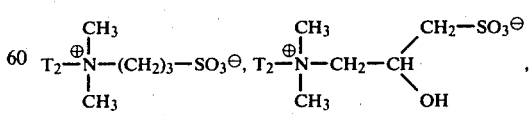

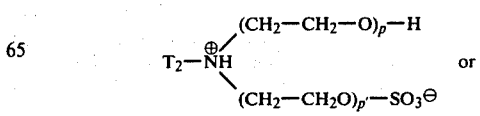

-continued

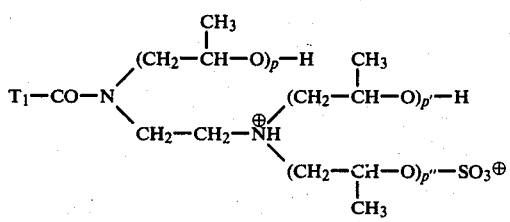

in which $T_1$ is alkyl or alkenyl having 7 to 21 carbon atoms, $T_2$ is alkyl or alkenyl having 8 to 22 carbon atoms and p, p' and p" are each an integer from 1 to 50.

13. A process for the preparation of a composition of claim 1, comprising the steps of polymerizing the monomer of the formula

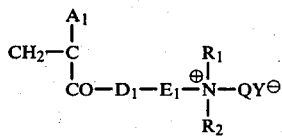

and optionally at least one of the comonomers of the formulae

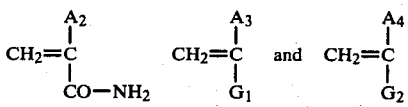

by water-in-oil emulsion polymerization in the presence of a water-in-oil emulsifier and optionally an emulsion stabilizer, or by solution polymerization, in each case in the presence of a polymerization initiator, to give component (a), precipitating the the polymer with a solvent which is soluble both in water and in oil, and drying the resulting polymer for use as as component (a), and mixing component (a) with component (b), at room temperature and at a pH value of 5 to 9.

14. A composition of claim 1, which contains 0.05 to 1.5 parts by weight of component (a), 5 to 20 parts by weight of component (b) diluted to a total of 100 parts by weight with demineralized water.

15. A composition of claim 14, which is adjusted to a pH value of 5 to 8 with an aqueous solution of sodium hydroxide or citric acid.

16. A hair treatment method, which comprises the steps of applying an effective amount of a composition of claim 14 to hair, which has been dampened with tapwater, at 20° to 40° C. and then shampooing and conditioning the hair.

17. Wig hair which has been treated by the method of claim 16.

* * * * *